(12) United States Patent
Sankaran et al.

(10) Patent No.: US 9,868,797 B2
(45) Date of Patent: Jan. 16, 2018

(54) BRIDGED METALLOCENE COMPLEX FOR OLEFIN POLYMERIZATION

(71) Applicants: SAUDI BASIC INDUSTRIES CORPORATION, Riyadh (SA); SABIC GLOBAL TECHNOLOGIES B.V., Bergen op Zoom (NL)

(72) Inventors: Nedumbamana Sankaran, Bangalore (IN); Prashant Sukumar Shinge, Bangalore (IN); Sharankumar Shetty, Bangalore (IN); Girish Chandra, Bangalore (IN); Haif Al-Shammari, Riyadh (SA); Abdulaziz Hamad Al-Humydi, Riyadh (SA); Edward Joseph Nesakumar, Bangalore (IN)

(73) Assignees: SAUDI BASIC INDUSTRIES CORPORATION, Riyadh (SA); SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 14/907,923

(22) PCT Filed: Jul. 29, 2014

(86) PCT No.: PCT/EP2014/066265
§ 371 (c)(1),
(2) Date: Jan. 27, 2016

(87) PCT Pub. No.: WO2015/014832
PCT Pub. Date: Feb. 5, 2015

(65) Prior Publication Data
US 2016/0168280 A1 Jun. 16, 2016

Related U.S. Application Data

(60) Provisional application No. 61/929,291, filed on Jan. 20, 2014.

(30) Foreign Application Priority Data

Aug. 1, 2013 (EP) .................................... 13178970

(51) Int. Cl.
*C07F 17/00* (2006.01)
*C08F 4/6592* (2006.01)
(Continued)

(52) U.S. Cl.
CPC .............. *C08F 4/76* (2013.01); *C07C 211/48* (2013.01); *C07C 211/52* (2013.01); *C07F 5/02* (2013.01); *C07F 5/025* (2013.01); *C07F 17/00* (2013.01); *C08F 4/6592* (2013.01); *C08F 10/02* (2013.01); *C07C 2602/08* (2017.05); *C08F 4/65908* (2013.01); *C08F 4/65912* (2013.01); *C08F 4/65916* (2013.01); *C08F 2420/02* (2013.01)

(58) Field of Classification Search
CPC ............................... C07F 17/00; C08F 4/6592
See application file for complete search history.

(56) References Cited

U.S. PATENT DOCUMENTS 5,272,236 A 12/1993 Lai et al.
6,342,622 B1 1/2002 Arts et al.
(Continued)

FOREIGN PATENT DOCUMENTS

KR 2010113336 A 10/2010
WO 9411406A1 A1 5/1994
(Continued)

OTHER PUBLICATIONS

International Search Report for PCT/EP2014/066265 dated Aug. 28, 2014, 8 pages.
Written Opinion of the ISR for PCT/EP2014/066265 dated Aug. 28, 2014, 9 pages.
Cho, Dae Joon, et al, "o-Phenylene-Bridged Cp/Amido Titanium Complexes for Ethylene/1-Hexene Copolymerizations", Organometallics 2006, 25, 2133-2134.
(Continued)

*Primary Examiner* — Caixia Lu
(74) *Attorney, Agent, or Firm* — Cantor Colburn LLP

(57) ABSTRACT

A metallocene complex according to formula 1

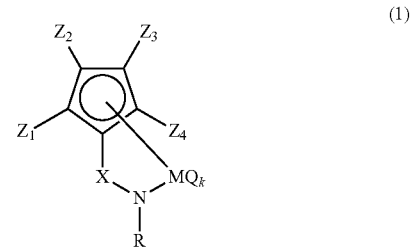

wherein
M is a metal selected from lanthanides or transition metals from group 3, 4, 5, or 6,
Q is an anionic ligand to M,
k is the number of Q groups and equals the valence of M minus 2,
X is a cyclic bridging group that is bonded to a carbon atom of the cyclopentadienyl ligand and to nitrogen,
$Z_1$, and $Z_4$ are hydrogen or a hydrocarbon radical with 1-20 carbon atoms; adjacent substituents $Z_2$ and $Z_3$ and are connected to form an indenyl or tetrahydroindenyl ring system and
R is hydrogen or a hydrocarbon radical with 1-20 carbon atoms.
Also described is a composition comprising the metallocene complex, a process for the preparation of the complex, and a process for the polymerization of olefin polymers in the presence of the metallocene complex.

15 Claims, No Drawings

(51) Int. Cl.
 *C08F 10/00* (2006.01)
 *C08F 4/76* (2006.01)
 *C07C 211/48* (2006.01)
 *C07F 5/02* (2006.01)
 *C07C 211/52* (2006.01)
 *C08F 10/02* (2006.01)
 *C08F 4/659* (2006.01)

(56) References Cited

U.S. PATENT DOCUMENTS 9,000,200 B2 * 4/2015 Al-Humydi ............ C07C 1/321
 556/53
2001/0014725 A1 * 8/2001 Becke ................... C07C 17/10
 526/126
2011/0177935 A1 * 7/2011 Lee ........................ C07F 17/00
 502/124

FOREIGN PATENT DOCUMENTS

WO 2007078133 A1 7/2007
WO 2007078134 A1 7/2007
WO 2008084931 A1 7/2008

OTHER PUBLICATIONS

Hayakawa, Junpei et al: "Material comprising polycyclic aromatic compound, organic electroluminescent device, and ink composition therefor", XP002728615, retrieved from STN Database accession No. 2012:194644 (Abstract only).

Lee, Sang Hoon, et al., "o-Phenylene-bridged Cp/amido titanium and zirconium complexes and their polymerization reactivity", Journal of Organometallic Chemistry 693 (2008) 457-467.

Tamano, Michiko et al: "Diarylaminopyrene material, organic electroluminescent device, and ink composition thereof", XP002728613, retrieved from STN Database accession No. 2011:996651 (abstract only).

Wu, Chun Ji, et al., "CO 2-Mediated ortho-Lithiation of N-Alkylanilines and its Use for the Construction of Polymerization Catalysts", Organometallics, vol. 27, No. 15, Jul. 17, 2008, 3907-3917.

Yang, Jye-Shane, et al., Excited-State Behavior of N-Phenyl-Substituted trans-3-Aminostilbenes: Where the "m-Amino Effect" Meets the "Amino-Conjugation Effect", J. Phys. Chem. A 2005, 109, 6450-6456.

* cited by examiner

BRIDGED METALLOCENE COMPLEX FOR OLEFIN POLYMERIZATION

This application is a national stage application of PCT/EP2014/066265 filed Jul. 29, 2014, which claims priority to U.S. Provisional Application 61/929,291 filed Jan. 20, 2014, and European Application EP 13178970.3 filed Aug. 1, 2013, which are hereby incorporated by reference in their entirety.

The invention relates to a metallocene complex, a process to prepare a metallocene complex, ligands to prepare the metallocene complex and a process to produce olefin polymers by polymerizing one or more olefins in the presence of a catalyst comprising the metallocene complex and to polyolefin, preferably polyethylene, obtainable by copolymerizing ethylene and at least one other olefin in the presence of the metallocene complex and to a polyolefin obtainable by polymerization using said metallocene complex.

The industrial use of metallocene complexes is not well established due to difficulties faced in metallocene synthesis and polyolefin production process. However, there is a growing interest in implementing metallocene complexes for the synthesis of polyolefins, preferably polyethylenes in the industry.

Bridged metallocene complexes are known in the state of the art and are for instance described in WO94/11406A1 and in U.S. Pat. No. 6,342,622. In these two patent publications metallocene complexes are described comprising two cyclopentadienyl or indenyl ligands that are bridged with a bridging group comprising sp3 or sp2 hybridized carbon atoms.

In U.S. Pat. No. 5,272,236 a different class of metallocene complexes is described comprising one cyclopentadienyl ligand connected via a bridge with a heteroatom, chosen from oxygen, sulfur, nitrogen or phosphorus. This heteroatom is also bonded to the metal in the metallocene complex. The bridging group can comprise carbon atoms, silicon atoms, germanium atoms and boron atoms.

WO2008/084931 discloses transition metal complexes comprising a bidentate ligand having a monocyclopentadienyl group coupled to an amido group. Examples of monocyclopentadienyl groups are cyclopentadienyl, 1-indenyl and fluorenyl groups.

A new family of bridged metallocene complexes has now been discovered which advantageously can be used for olefin polymerization, preferably for ethylene polymerization, more preferably for the copolymerization of ethylene with another olefin.

It has been surprisingly discovered that the incorporation of other olefins into the ethylene backbone may be improved when these metallocene complexes were used in ethylene copolymerisation. This has the advantage that ethylene copolymers with a lower density can be obtained. Additionally, the complexes may show improved catalytic activity towards ethylene and/or alfa-olefins. Depending on the kinetic profile of the complexes, this may result in high initial activity, which can reduce the reaction times to prepare polyolefins, or in stable catalytic performance, which may lower the exothermicity of the polymerization reaction when using the metallocene complexes according to the invention as compared to known metallocene complexes.

Metallocene Complex

The metallocene complexes according to the invention are metallocene complexes according to formula 1

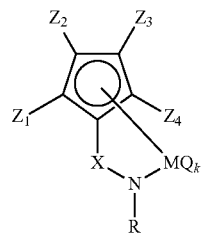

wherein
M is a metal selected from lanthanides or transition metals from group 3, 4, 5 or 6 of the Periodic System of the Elements,
Q is an anionic ligand to M,
k is the number of Q groups and equals the valence of M minus 2,
X is a cyclic bridging group,
$Z_1$ and $L_4$ are identical or different and can be chosen from the group consisting of hydrogen and a hydrocarbon radical with 1-20 carbon atoms; adjacent substituents $Z_2$ and $Z_3$ are connected to form an indenyl or tetrahydroindenyl ring system together with the carbon atoms of the Cp ring to which they are hound and
R is chosen from the group consisting of hydrogen and a hydrocarbon radical with 1-20 carbon atoms.

The metallocene complex according to the invention comprises a metal selected from lanthanides or transition metals from group 3, 4, 5 or 6 of the Periodic System of the Elements. The Periodic System of the Elements is understood to be the Periodic System of the Elements that can be found at www.chemicool.com. The metal M is preferably chosen from the group consisting of Ti, Zr, Hf, V and Sm, more preferably from Ti, Zr and Hf, most preferably the metal is Zr.

Q is an anionic ligand to M. The Q ligands preferably are the same and are selected from the group consisting of halogen (F, Cl, Br, I) and hydrocarbyl groups comprising 1 to 20 carbon atoms. More preferably the ligands are Cl or a methyl group.

k is the number of Q groups and equals the valence of M minus 2; k is an integer. Preferably, k is 2.

X is a cyclic bridging group. X is bridging between a carbon atom of the cyclopentadienyl ligand and nitrogen. X can contain both sp3 and sp2 hybridized carbon atoms. The cyclic bridging group X can be monocyclic or polycyclic. The cyclic bridging group X may comprise fused rings. Examples of cyclic bridging groups are phenylene, cyclopropylene, cyclobutylene, cyclopentylene, cyclohexylene, cyclohexenylene, cyclohexadienylene, tolylene, benzylene, naphthylene, anthrylene, pyrenylene, biphenylene and binaphthylene. The cyclic bridging group can be substituted with alkyl groups having 1 to 10 carbon atoms, for example the substituents may be selected from the group of methyl, ethyl, n-propyl, n-butyl, n-pentyl or n-hexyl. Preferably, X carries less than 10 substituents, more preferably less than 5 substituents and most preferably no substituents. X preferably is chosen from the group consisting of a phenylene and a biphenylene group. Most preferably X is chosen from the group consisting of a 1,2 phenylene group and a 2,2'-biphenylene group.

$Z_1$ and $Z_4$ are identical or different and can be chosen from the group of hydrogen and a hydrocarbon radical with 1-20 carbon atoms. Hydrocarbon radicals can be alkyl, aryl or aryl alkyl substituents. Examples of alkyl groups are methyl, ethyl, propyl, butyl, hexyl and decyl. Examples of aryl groups are phenyl, mesityl, tolyl, and cumenyl. Examples of aryl alkyl substituents are benzyl, pentamethylbenzyl, xylyl, styryl and trityl.

Adjacent substituents $Z_2$ and $Z_3$ are connected to form an indenyl or tetrahydroindenyl ring system together with the carbon atoms of the Cp ring to which they are bound. $Z_2$ and $Z_3$ are connected to form 6 membered ring such as phenyl, substituted phenyls, hydrogenated phenyls or substituted hydrogenated phenyls, wherein preferred substitutions are alkyl groups, as part of an indenyl or tetrahydroindenyl ring system.

Preferably $Z_1$ and $Z_4$ are hydrogen. Most preferably $Z_1$ and $Z_4$ are hydrogen and $Z_2$ and $Z_3$ are connected, such that a 2-indenyl ligand or a 2-tetrahydroindenyl ligand is formed.

R is chosen from the group of hydrogen and a hydrocarbon radical with 1-20 carbon atoms. Hydrocarbon radicals can be alkyl, aryl or aryl alkyl substituents. Examples of alkyl groups are methyl, ethyl, propyl, butyl, hexyl and decyl. Examples of aryl groups are phenyl, mesityl, tolyl, and cumenyl. Examples of aryl alkyl substituents are benzyl, pentamethylbenzyl, xylyl, styryl and trityl. R is preferably an alkyl group with 1-10 carbon atoms, more preferably with 1-6 carbon atoms. Preferably R is a branched alkyl, more preferably R is isopropyl or t-butyl. Most preferably R is a t-butyl group.

Preferred Metallocenes

In a preferred embodiment of the invention, the metallocene complex is according to formula 2

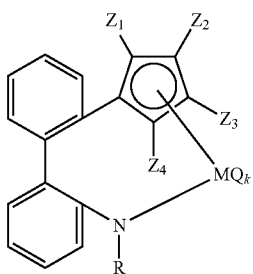

(2)

wherein M is chosen from the group of Ti, Zr and Hf, and wherein $Z_1$ and $Z_4$ are identical or different and can be chosen from the group consisting of hydrogen or a hydrocarbon radical with 1-20 carbon atoms; adjacent substituents $Z_2$ and $Z_3$ are connected to form an indenyl or tetrahydroindenyl ring system together with the carbon atoms of the Cp ring to which they are bound and R is chosen from the group consisting of hydrogen and a hydrocarbon radical with 1-20 carbon atoms, preferably R is a t-butyl group; Q is Cl or a methyl group; and k is the number of Q groups and equals the valence of M minus 2; k is an integer.

In another preferred embodiment the invention relates to a metallocene complex according to formula 3

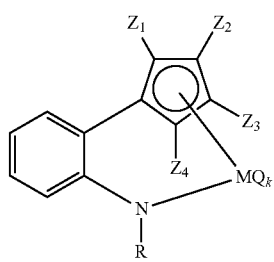

(3)

wherein M is chosen from the group of Ti, Zr and Hf, and wherein $Z_1$ and $Z_4$ are identical or different and can be chosen from the group consisting of hydrogen or a hydrocarbon radical with 1-20 carbon atoms; adjacent substituents $Z_2$ and $Z_3$ are connected to form an indenyl or tetrahydroindenyl ring system together with the carbon atoms of the Cp ring to which they are bound and R is chosen from the group consisting of hydrogen and a hydrocarbon radical with 1-20 carbon atoms, preferably R is a t-butyl group; Q is Cl or a methyl group; and k is the number of Q groups and equals the valence of M minus 2; k is an integer.

In a preferred embodiment of the invention the metallocene complex contains a 2-indenyl group and is represented by the formula 4

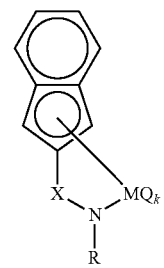

(4)

wherein M is chosen from the group of Ti, Zr and Hf, and wherein X is a cyclic bridging group, R is chosen from the group consisting of hydrogen and a hydrocarbon radical with 1-20 carbon atoms; Q is Cl or a methyl group; and k is the number of Q groups and equals the valence of M minus 2; k is an integer. Most preferably M is Zr, R is t-butyl, Q is Cl or methyl, k=2 and X is chosen from the group consisting of phenylene, cyclopropylene, cyclobutylene, cyclopentylene, cyclohexylene, cyclohexenylene, cyclohexadienylene, tolylene, benzylene, naphthylene, anthrylene, pyrenylene, biphenylene and binaphthylene, most preferably X is chosen from the group of 1,2-phenylene and 2,2'-biphenylene.

In yet another preferred embodiment of the invention, the metallocene complex is according to formula 5

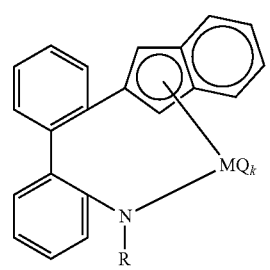

(5)

wherein M is chosen from the group of Ti, Zr and Hf, and wherein R is chosen from the group of hydrogen and a hydrocarbon radical with 1-20 carbon atoms, preferably R is a t-butyl group; Q is Cl or a methyl group; and k is the number of Q groups and equals the valence of M minus 2; k is an integer. Most preferably M is Zr, R is t-butyl, Q is Cl or methyl and k=2.

In yet another preferred embodiment of the invention, the metallocene complex is according to formula 6

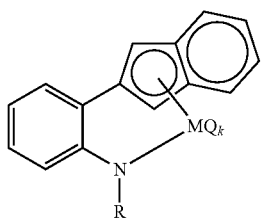

(6)

wherein M is chosen from the group of Ti, Zr and Hf, and wherein R is chosen from the group of hydrogen and a hydrocarbon radical with 1-20 carbon atoms, preferably R is a t-butyl group; Q is Cl or a methyl group; and k is the number of Q groups and equals the valence of M minus 2; k is an integer.

Most preferably M is Zr, R is t-butyl, Q is Cl or methyl and k=2.

Support

The metallocene complex can be supported on a support. The support is preferably an inert support, more preferably a porous inert support. Examples of porous inert supports materials are talc and inorganic oxides. Preferably, the support material is in a finely divided form.

Therefore, the invention also relates to a composition comprising the metallocene complex of the invention and a support on which the metallocene complex is present.

Suitable inorganic oxide materials include group 2A, 3A, 4A and 4B metal oxides such as silica, alumina and mixtures thereof. Other inorganic oxides that may be employed either alone or in combination with the silica or alumina are magnesia, titania, zirconia and the like. Other support materials, however, can be employed, for example finely divided functionalized polyolefins such as finely divided polyethylene.

Preferably, the support is a silica having a surface area between 200 and 900 m²/g and a pore volume between 0.5 and 4 ml/g.

Ligands, Intermediates and Ligand Precursor

The invention also relates to a process for making ligands and metallocene complex. The ligands can be prepared in a multiple step process. First an intermediate 1 (Formula 7) is prepared by reacting compounds in a solvent at a pH above 7 according to the following scheme:

Scheme 1. Synthesis of intermediate 1 (Formula 7)

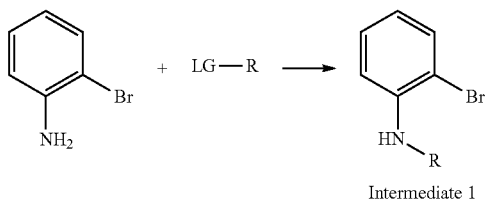

(7)

Intermediate 1

LG is a leaving group. Examples of LG are halides, like for example Cl or Br, or 2,2,2-trichloroacetimidate group.

R is chosen from the group consisting of hydrogen and a hydrocarbon radical with 1-20 carbon atoms, preferably R is a t-butyl group.

This intermediate 1 can react with a compound LF—B(OH)$_2$, in the presence of a Pd catalyst and a Lewis base (according to a Suzuki reaction), to arrive at a ligand precursor according to the following scheme:

Scheme 2 synthesis of ligand percursor.

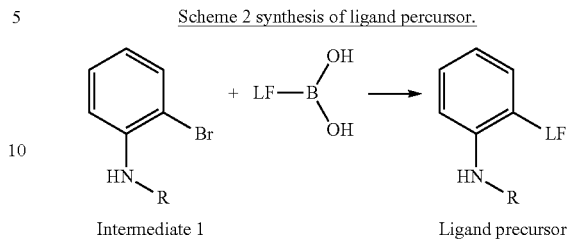

Intermediate 1                                      Ligand precursor

LF is a ligand fragment, which is chosen from the group consisting of

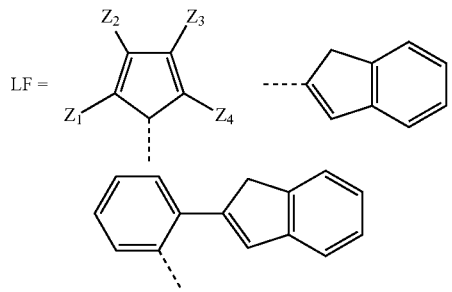

wherein $Z_1$ and $Z_4$ are identical or different and can be chosen from the group consisting of hydrogen or a hydrocarbon radical with 1-20 carbon atoms; adjacent substituents $Z_2$ and $Z_3$ are connected to form an indenyl or tetrahydroindenyl ring system together with the carbon atoms of the Cp ring to which they are bound and R is chosen from the group consisting of hydrogen and a hydrocarbon radical with 1-20 carbon atoms, preferably R is a t-butyl group.

The invention relates to a ligand precursor having a structure according to formula 8

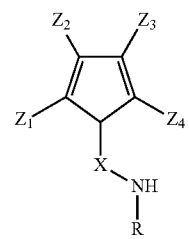

(8)

wherein X is a cyclic bridging group; $Z_1$ and $Z_4$ are identical or different and can be chosen from the group consisting of hydrogen or a hydrocarbon radical with 1-20 carbon atoms; adjacent substituents $Z_2$ and $Z_3$ are connected to form an indenyl or tetrahydroindenyl ring system together with the carbon atoms of the Cp ring to which they are bound; and R is chosen from the group consisting of hydrogen and a hydrocarbon radical with 1-20 carbon atoms, preferably R is a t-butyl group.

The invention also relates to a preferred ligand precursor having a structure according to formula 9:

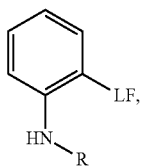
(9)

wherein LF is a ligand fragment, which is chosen from the group consisting of

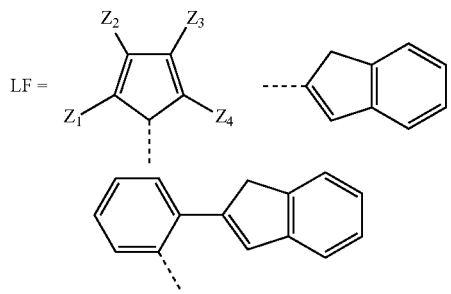

wherein $Z_1$ and $Z_4$ are identical or different and can be chosen from the group consisting of hydrogen or a hydrocarbon radical with 1-20 carbon atoms; adjacent substituents $Z_2$ and $Z_3$ are connected to form an indenyl or tetrahydroindenyl ring system together with the carbon atoms of the Cp ring to which they are bound and R is chosen from the group consisting of hydrogen and a hydrocarbon radical with 1-20 carbon atoms.

In a preferred embodiment the ligand precursor has a structure according to formula 10 or 11

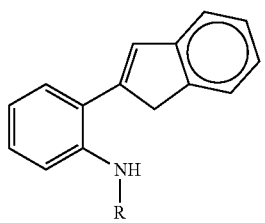
(10)

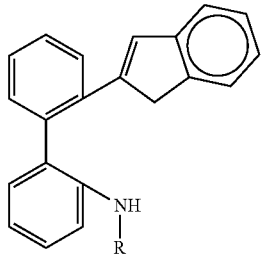
(11)

R is chosen from the group consisting of hydrogen and a hydrocarbon radical with 1-20 carbon atoms, preferably a t-butyl group.

Metallocene Complex Synthesis.

The invention also relates to the preparation of metallocene complexes according to formula 1, by
  a. creating anions of the ligand precursors according to formula 8 with an organic or inorganic base,
  b. reacting the anion of the ligand precursor with $(Me_2N)_aMQ_k$, wherein Me is methyl, M is a metal selected from lanthanides or transition metals from group 3, 4, 5 or 6 of the Periodic System of the Elements, Q is an anionic ligand to M, k is the number of Q groups and equals the valence of M minus 2 and a equals the valence of M minus k, to yield a metallocene complex according to formula 1.

Examples of organic and inorganic bases that can be used for creating anions of the ligand precursors are methyllithium, butyllithium, sec-butyllithium, t-butyllithium, lithiumdiisopropylamide (LDA), sodiumhydride, isopropylmagnesiumchloridelithiumchloride, s-butylmagnesiumchloride, sodiumhexamethyldisilazide, potassiumhexamethyldisilazide and combinations thereof.

Metallocene complexes according to formula 12 can be obtained when the following preferred process for the preparation is used.

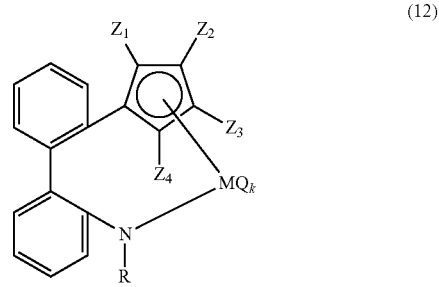
(12)

In a general procedure for the synthesis of the complex of formula 12, n-BuLi was added to a cooled solution of the ligand precursor (formula 10 or 11) in freshly dried diethyl ether under N2 atmosphere at −78° C. The cold bath was removed after ~30 min and solution was stirred at room temperature for 4 hrs. The solution was now again cooled to −78° C. and solid $ZrCl_4$ was added. The solution was slowly brought to room temperature and further stirred for 2 h. The solvent was then removed by filtration and the residue was washed with ether.

A specific example of the preparation of the metallocene complexes according to formula 5 comprises the steps of:
  a. reacting 2-bromophenyl boronic acid with 1,8-diaminonaphthalene to form a protected compound (formula 13),

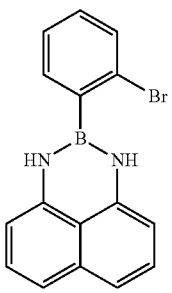
(13)

b. reacting the protected compound (13) with a compound with the formula 14,

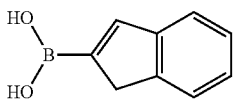

(14)

in the presence of a Pd catalyst and in the presence of a base (with a reaction known as the Suzuki reaction), herewith forming a protected compound according to formula 15

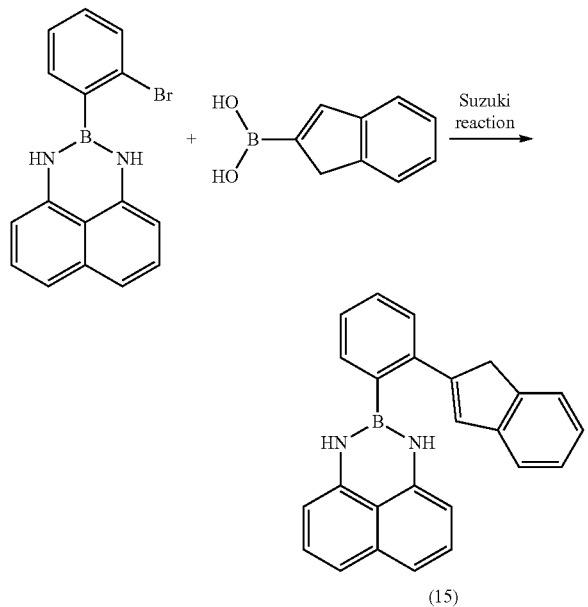

(15)

c. deprotecting the protected compound by reaction with an acid to arrive at the compound according to formula 16,

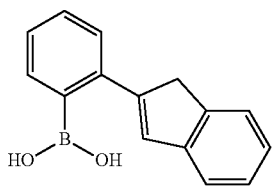

(16)

d. reacting the compound (formula 16) with N-substituted 2-bromoaniline (formula 7) in the presence of a Pd catalyst in the presence of a base (according to the Suzuki reaction), to form a ligand precursor (formula 11), wherein the substituent R of the N in 2-bromoaniline is chosen from the group of hydrogen and a hydrocarbon radical with 1-20 carbon atoms, preferably t-butyl e. creating anions of the ligand precursors (11) with an organic or inorganic base f. reacting the anion of the ligand precursor with $(Me_2N)_aMQ_k$, wherein Me is methyl; M is a metal selected from lanthanides or transition metals from group 3, 4, 5 or 6 of the Periodic System of the Elements, preferably M is Zr; Q is an anionic ligand to M, preferably Q is Cl or methyl; k is the number of Q groups and equals the valence of M minus 2; and a equals the valence of M minus k, to yield a metallocene complex according to formula 5.

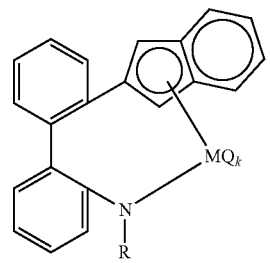

(5)

Olefin Polymerization.

In another aspect, the invention relates to a process for the preparation of olefin polymers by polymerizing one or more olefins in the presence of the metallocene complex of the invention or in the presence of the composition of the invention, wherein the metallocene complex is present on a support and a cocatalyst The cocatalyst employed according to the present invention include aluminium- or boron-containing cocatalysts. Suitable aluminium-containing cocatalysts comprise aluminoxanes and alkyl aluminium. The aluminoxanes usable according to the present invention are well known and preferably comprise oligomeric linear and/or cyclic alkyl aluminoxanes represented by the formula: $R^3$—$(AlR^3$—$O)_n$—$AlR^3{}_2$ for oligomeric, linear aluminoxanes and $(-AlR^3-O-)_m$ for oligomeric, cyclic aluminoxanes; wherein n is 1-40, preferably n is 10-20; m is 3-40, preferably m is 3-20 and $R^3$ is a $C_1$ to $C_8$ alkyl group and preferably a methyl group. Further other organoaluminum compounds can be used such as trimethylaluminum, triethylaluminum, triisopropylaluminum, tri-n-propylaluminum, triisobutylaluminum, tri-n-butylaluminum, triamylaluminium; dimethylaluminium ethoxide, diethylaluminium ethoxide, diisopropylaluminium ethoxide, di-n-propylaluminium ethoxide, diisobutylaluminium ethoxide and di-n-butylaluminium ethoxide; dimethylaluminium hydride, diethylaluminium hydride, diisopropylaluminium hydride, di-n-propylaluminium hydride, diisobutylaluminium hydride and di-n-butylaluminium hydride.

Suitable boron-containing cocatalysts include trialkylboranes, for example trimethylborane or triethylborane and/or perfluorophenylborane and/or a perfluorophenylborate.

In the process to produce olefin polymers by polymerizing one or more olefins in the presence of a metallocene complex preferably an organoaluminum cocatalyst is present.

More preferably, methylaluminoxane is used as the cocatalyst.

The process to produce the olefin polymers may start with the reaction of the metallocene complex according to the invention with the cocatalyst. This reaction can be performed in the same vessel as the reaction vessel wherein the olefin polymers are produced or in a separate vessel, whereafter the mixture of the metallocene complex and the cocatalyst is fed to the reaction vessel. During the reaction described above an inert solvent can be used.

In the mixture of the metallocene complex and the cocatalyst, the cocatalyst is used in an amount of 10 to 100,000 mol, preferably from 10 to 10,000 mol per mol of the transition metal compound.

The solvent used in the process to produce olefin polymers may be any organic solvent usually used for the polymerization. Examples of solvents are benzene, toluene, xylene, butane, pentane, hexane, heptane, cyclohexane and methylene chloride. Also the olefin to be polymerized can be used as the solvent.

In the process to produce olefin polymers the polymerization conditions, like for example temperature, time, pressure, monomer concentration can be chosen within wide limits. The polymerization temperature is in the range from −100 to 300° C., preferably 0 to 200° C., more preferably 10 to 100° C. The polymerization time is in the range of from 10 seconds to 20 hours, preferably from 1 minute to 10 hours, more preferably from 5 minutes to 5 hours. The ethylene pressure during polymerization is in the range from 1 to 3500 bar, preferably from 1 to 2500 bar, more preferably from 1 to 1000 bar, even more preferably from 1 to 500 bar, most preferably from 1 to 100 bar. The molecular weight of the polymer can be controlled by use of hydrogen in the polymerization. The polymerization may be conducted by a batch process, semicontinuous process or a continuous process and may also be conducted in two or more steps of different polymerization conditions. The polyolefin produced is separated from the polymerization solvent and dried by methods known to a person skilled in the art.

In the process to produce olefin polymers the olefin which is polymerized can be one type of olefin or can be mixtures of different olefins. The polymerization thus includes homopolymerization and copolymerization. Examples of olefins are α-olefins such as ethylene, propylene, 1-butene, 1-pentene, 4-methyl-1-pentene, 1-hexene, 1-octene, 1-nonene, 1-decene and styrene; conjugated and non-conjugated dienes such as butadiene, 1,4-hexadiene, 5-ethylidene-2-norbornene, dicyclopentadiene, 4-methyl-1,4-hexadiene and 7-methyl-1,6-octadiene; and cyclic olefins such as cyclobutene, but is not limited thereto.

Preferably, at least one of the olefins that is polymerized is ethylene. More preferably, a mixture of ethylene and at least one other olefin of 3 or more carbon atoms is polymerized.

In particular, in the production of LLDPE obtained by copolymerizing ethylene and at least one other olefin of 3 or more carbon atoms a high molecular weight of the olefin polymer can be obtained. Preferably, the other olefin of 3 or more carbon atoms is chosen from 1-butene, 1-hexene or 1-octene, more preferably the other olefin is 1-hexene.

Preferably, the olefin comonomer is present in an amount of about 5 to about 20 percent by weight of the ethylene-olefin copolymer, more preferably an amount of from about 7 to about 15 percent by weight of the ethylene-alpha olefin copolymer.

For example an LLDPE having a melt mass flow rate (also known as melt flow index) as determined using ASTM D1238-10 (190° C./2.16 kg) which ranges from 1 to 125 g/10 min and a density in the range from 900 kg/m$^3$ to less than 940 kg/m$^3$ as determined using ASTM D1505-10 may be obtained. For example, the density of the linear low density polyethylene ranges from about 915 kg/m$^3$ to less than 940 kg/m$^3$, for example between 915 and 925 kg/m$^3$.

For example, the melt flow index of the linear low density polyethylene ranges from 0.3 to 3 g/10 min, for example from 0.5 to 1.5 g/10 min.

The polymerisation may be performed via a gas phase process or via a slurry process.

The production processes of polyethylene are summarised in "Handbook of Polyethylene" by Andrew Peacock (2000; Dekker; ISBN 0824795466) at pages 43-66. The catalysts can be divided in three different subclasses including Ziegler Natta catalysts, Phillips catalysts and single site catalysts. The latter class is a family of different classes of compounds, metallocene catalysts being one of them. As elucidated at pages 53-54 of said Handbook a Ziegler-Natta catalysed polymer is obtained via the interaction of an organometallic compound or hydride of a Group I-III metal with a derivative of a Group IV-VIII transition metal. An example of a (modified) Ziegler-Natta catalyst is a catalyst based on titanium tetra chloride and the organometallic compound triethylaluminium. A difference between metallocene catalysts and Ziegler Natta catalysts is the distribution of active sites. Ziegler Natta catalysts are heterogeneous and have many active sites. Consequently polymers produced with these different catalysts will be different regarding for example the molecular weight distribution and the comonomer distribution.

The various processes may be divided into solution polymerisation processes employing homogeneous (soluble) catalysts and processes employing supported (heterogeneous) catalysts. The latter processes include both slurry and gas phase processes.

The invention is also directed to a polyolefin, for example polyethylene, preferably LLDPE obtainable or obtained by the process of the invention, for example by copolymerizing ethylene and at least one other olefin in the presence of a metallocene complex according to the invention or a composition, wherein the metallocene complex according to the invention is present on a support.

As defined herein, in linear low density polyethylene, the term "linear" means that the polymer lacks measurable or demonstrable long chain branches, that is, the polymer is substituted with an average of less than 0.01 long chain branch/1000 carbon atoms.

"Long chain branching" (LCB) means a chain length longer than the short chain branch that results from the incorporation of the α-olefin(s) into the polymer backbone. Each long chain branch will have the same comonomer distribution as the polymer backbones and can be as long as the polymer backbone to which it is attached.

As a practical matter, current $^{13}$C nuclear magnetic resonance spectroscopy cannot distinguish the length of a long chain branch in excess of six carbon atoms. However, there are other known techniques useful for determining the presence of long chain branches in ethylene polymers. Two such methods are gel permeation chromatography coupled with a low angle laser light scattering detector (GPC-LALLS) and gel permeation chromatography coupled with a differential viscometer detector (GPCDV). The use of these techniques for long chain branch detection and the underlying theories have been well documented in the literature.

See, for example, Zimm, G. H. and Stockmayer, W. H., J. Chem. Phys., 17:1301 (1949) and Rudin, A., Modern Methods of Polymer Characterization, John Wiley & Sons, New York (1991 pp. 103-112).

It has been found that with the metallocene complex of the invention or with the composition of the invention wherein the metallocene complex of the invention is present on a support, it is possible to produce polyethylene from ethylene and at least one other olefin, for example an olefin having up to 8 carbon atoms, with a high incorporation of the at least one other olefin.

The amount of incorporation of the at least one other olefin, for example an α-olefin in the polyethylene is expressed by the amount of branches per 1000 carbon atoms.

The presence of short chain branching of up to 6 carbon atoms in length can be determined in ethylene polymers by using $^{13}$C nuclear magnetic resonance (NMR) spectroscopy and is quantified using the method described by Randall (Rev. Macromol. Chem. Phys., C.29, V. 2 & 3, p. 285-297).

Therefore, the invention also relates to a polyolefin, preferably polyethylene, more preferably linear low density polyethylene (LLDPE). The low density polyethylene, for example LLDPE, preferably has an amount of branches per 1000 carbon atoms as determined using $^{13}$C NMR of at least 18, for example of at least 19, for example at least 20 and/or for example at most 30, for example at most 25, for example at most 23, for example at most 21. Preferably, said polyethylene is substituted with an average of less than 0.01 long chain branch per 1000 carbon atoms.

The number average molecular weight (Mn) of the polyolefin, for example polyethylene, for example LLDPE of the invention may vary between wide ranges and may for example be in the range from 1000 to 200000 Da.

For example, the Mn of the polyolefin of the invention may be at least 1500, for example at least 2000, for example at least 20,000, for example at least 50,000 and/or for example at most 150,000, for example at most 110,000, for example at most 100,000, for example at most 70,000.

The weight average molecular weight (Mw) of the polyolefin, for example polyethylene, for example LLDPE of the invention may also vary between wide ranges and may for example be in the range from 1500 to 500000. For example, the Mw of the polyolefin of the invention may be at least 2500, for example at least 10,000, for example at least 50,000, for example at least 100,000 and/or for example at most 400,000, for example at least 350,000, for example at most 300,000, for example at most 250,000.

For purpose of the invention, the Mw and Mn are determined using SEC (Size Exclusion Chromatography) using 1,2,4-trichlorobenzene as an eluent, and calibrated using linear polyethylene standards.

The molecular weight distribution (that is Mw/Mn) of the polyolefin of the invention may for example vary from 2 to 5, from 2.1 to 4 or from 2.5 to 3.5.

The crystallinity temperature (Tc) of the polyolefin of the invention may for example be in the range from 90 to 120° C. The melt temperature (Tm) of the polyolefin of the invention may for example be in the range from 100 to 140° C.

For purpose of the invention, the $T_m$ and $T_c$ are determined using Differential Scanning Calorimetry according to ASTM D 3418-08 using a scan rate of 10° C./min on a sample of 10 mg and using the second heating cycle The polyolefin obtained or obtainable by the process of the invention may be mixed with suitable additives.

Examples of suitable additives for polyethylene include but are not limited to the additives usually used for polyethylene, for example antioxidants, nucleating agents, acid scavengers, processing aids, lubricants, surfactants, blowing agents, ultraviolet light absorbers, quenchers, antistatic agents, slip agents, anti-blocking agents, antifogging agents, pigments, dyes and fillers, and cure agents such as peroxides. The additives may be present in the typically effective amounts well known in the art, such as 0.001 weight to 10 weight % based on the total composition.

The polyolefins of the invention and compositions comprising said polyolefins may suitably be used for the manufacture of articles. For example, the polyolefins and compositions of the invention may be manufactured into film, for example by compounding, extrusion, film blowing or casting or other methods of film formation to achieve, for example uniaxial or biaxial orientation. Examples of films include blown or cast films formed by coextrusion (to form multilayer films) or by lamination and may be useful as films for packaging, for example as shrink film, cling film, stretch film, sealing films, oriented films, snack packaging, heavy duty bags, grocery sacks, baked and frozen food packaging, medical packaging, industrial liners, membranes, etc. in food-contact and non-food contact applications, agricultural films and sheets.

Therefore, in another aspect, the invention also relates to articles comprising the polyolefins obtainable by the process of the invention.

In yet another aspect, the invention also relates to use of the polyolefins obtainable by the process of the invention for the preparation of articles, for example for the preparation of films.

In yet another aspect, the invention relates to a process for the preparation of articles using the polyolefin according to the invention.

Although the invention has been described in detail for purposes of illustration, it is understood that such detail is solely for that purpose and variations can be made therein by those skilled in the art without departing from the spirit and scope of the invention as defined in the claims.

It is further noted that the invention relates to all possible combinations of features described herein, preferred in particular are those combinations of features that are present in the claims.

It is further noted that the term 'comprising' does not exclude the presence of other elements. However, it is also to be understood that a description on a product comprising certain components also discloses a product consisting of these components. Similarly, it is also to be understood that a description on a process comprising certain steps also discloses a process consisting of these steps.

The invention will hereafter be elucidated by way of the following examples, without being limited thereto.

General remarks relating to the experiments which are performed.

Most of the materials were received from Aldrich. Indene-2-boronic acid was custom synthesized and supplied by Aldrich. The dry solvents used for the reaction were either dried in the lab using standard procedures or obtained from Merck Chemicals India Ltd. 2-bromoindene used in the reactions was procured from TCI, Japan. All materials and reagents used for analysis were of high purity. The reactions were monitored by thin layer chromatograpy (TLC) and High Performance Liquid Chromatography (HPLC). The compounds were purified by different techniques such as by column chromatography, by preparative TLC, by preparative HPLC or by crystallization. The purity of the compounds was analyzed by HPLC. Compounds were characterized by a liquid chromatograph-mass spectrometer (LC-MS) system, comprising a liquid chromatograph and a Quattro Ultima Pt mass spectrometer. An Xterra C18 (50 mm×4.6 mm; 5 microns) column was used for separating the components by liquid chromatography. $^a$H and $^{13}$C NMR spectra for all the compounds were recorded on a 300 MHz Bruker NMR spectrometer. CDCl3 was used as the solvent for NMR.

EXAMPLE 1

Step 1: Synthesis of 1-bromo-2-(N-tert-butyl)benzene-tert-butyl 2-bromoaniline Scheme 1

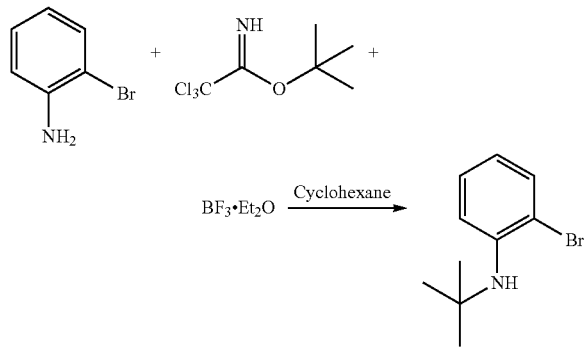

64 g (0.372 moles) of 2-bromoaniline was taken in 500 ml of cyclohexane and added to 200 g (0.915 moles) of tert-butyl-2,2,2-trichloroacetimiclate. BF3.ethereate (9.6 ml (25.8 ml/mol)) was added dropwise, slowly. Care was taken so that the reaction temperature did not rise above the room temperature. The reaction mixture was stirred at room temperature overnight. Next day, the precipitated salt was filtered off and the filtrate was concentrated. The concentrated fraction was purified by column chromatography using hexane as eluent. The impure fraction obtained after the first column was purified again on a second column. Yield: 83.5 g (97%).

Step 2: Synthesis of 1-(N-tert butyl)-2-(2-indenyl)benzene

Scheme 2

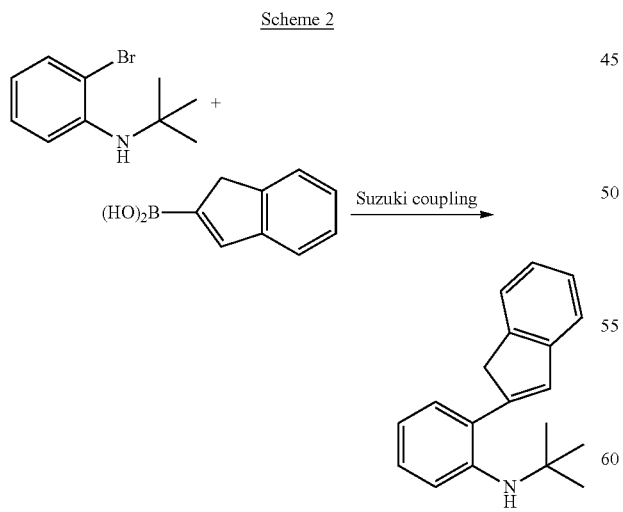

42 g (0.183 moles) of 1-bromo-2-(N-tert-butyl)benzene-tert-butyl 2-bromoaniline was dissolved in 400 ml of toluene and added to tetrakis triphenyl phosphine palladium (1.05 g; 0.000832 moles; 5 mol %). After 15 min, aqueous sodium carbonate (117 g; 1.098 moles, dissolved in 400 ml water) was added followed by the indene-2-boronic acid (34.3 g; 0.214 moles). The reaction mixture was stirred at 115° C. overnight. Next day, the reaction mixture was cooled and the organic layer was separated. The organic layer was concentrated and purified by column chromatography using hexane:dichloromethane as eluent (Gradient: 0-20% of dichloromethane). Yield: 21 g (44%).

500 mg (0.0019 moles) of the ligand was weighed into one arm of a clean, dry double Schlenk (inside the glove box). The Schlenk was transferred into fumehood and N2 atmosphere was applied. Freshly dried diethyl ether (15 ml) was added using a syringe. The sample was dissolved completely in diethyl ether. The solution was cooled to −78° C. n-BuLi (2.49 ml; 1.6N in hexanes; 0.00399 moles) was added to this solution drop wise.

The color gradually changed to yellow and the solution became hazy. The cold bath was removed after ~30 min and solution left to stir at RT for 4 hrs. The solution became clear and the color of the solution gradually became brown with a greenish tinch. The solution was again cooled to −78° C. and solid ZrCl4 (0.442 g; 0.0019 moles) was added. The temperature of the solution was slowly brought to RT and left the solution for stirring for 2 h. The color of the solution was turned to brown and solid was precipitated. Stopped the stirring and ether was taken to the other arm of the Schlenk by filtration. Solid was washed with ether and dried.

EXAMPLE 2

Synthesis of Protected 2-Bromophenyl Boronic Acid

The reaction for the preparation of 1-bromo-2-(N-tert-butyl)benzene-tert-butyl 2-bromoaniline was performed as in example 1, step 1 above.

Synthesis of Protected 2-Bromophenyl Boronic Acid

Scheme 3

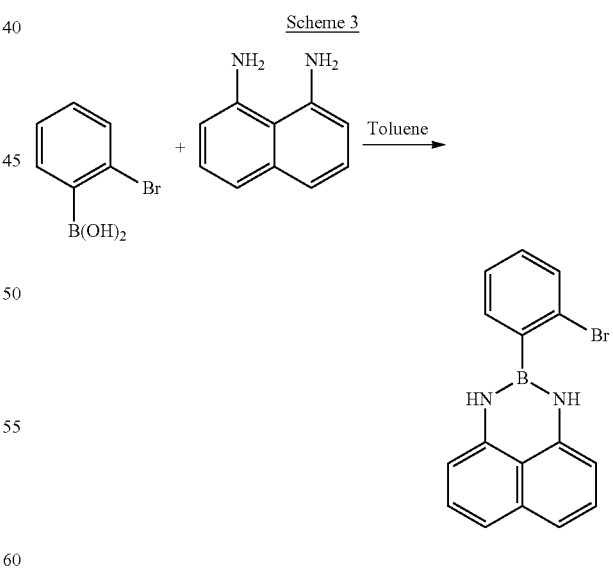

100 g (0.498 moles) of 2-bromophenyl boronic acid was taken in toluene (2 L) and added to 86.6 g (0.548 moles) of 1,8-diaminonaphthalene. The reaction mixture was refluxed and distilled using a Dean-Stark apparatus. The volume was reduced to 100 ml and the reaction mixture was cooled. The cooled mixture was recrystallized from hexane. Yield: 152 g (95%).

EXAMPLE 3

Synthesis of 2-(2-Indenyl) Substituted Protected Phenylboronic Acid 2-(2-indenyl) substituted protected phenylboronic acid is synthesized according to the following scheme 4:

Scheme 4

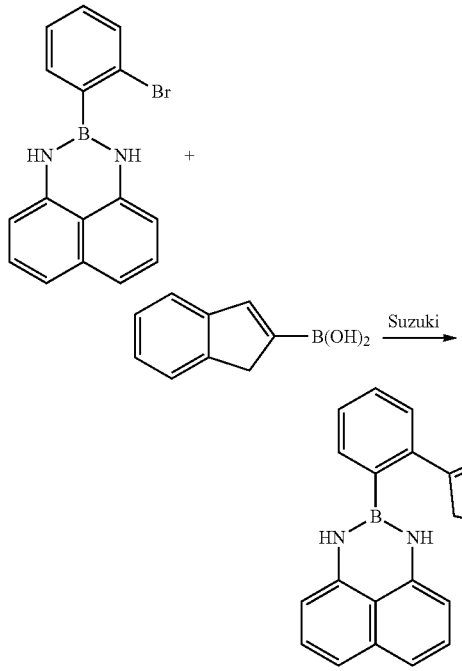

170 g (0.526 moles) of the protected 2-bromophenyl noronic prepared in accordance with example 2) acid was taken in toluene (1.5 L) and added to 3.043 g (0.00263 moles; 5 mol %) of tetrakis triphenyl phosphine palladium. The mixture was stirred for 15 min and added to aqueous sodium carbonate (340 g, 3.2075 moles). Indene-2-boronic acid (101 g, 0.6312 moles) was now added and the reaction mixture was stirred overnight at reflux. The product started to precipitate in the reaction flask. Next day, the reaction mixture was cooled. The precipitated product was filtered, washed with plenty of water and dried. Yield: 183 g (97%).

EXAMPLE 4

Synthesis of 2-(2-Indenyl)Phenylboronic Acid 2-(2-indenyl)phenylboronic acid is synthesized according to scheme 5:

Scheme 5

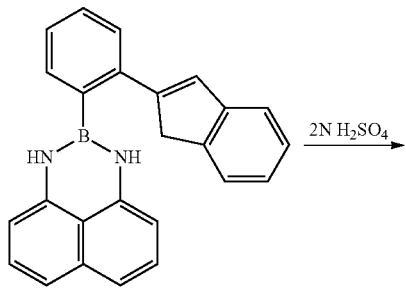

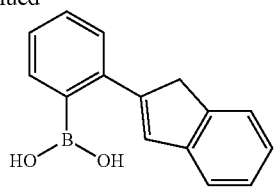

182 g (0.508 moles) of 2-(2-indenyl) substituted protected phenylboronic acid (prepared according to example 3) was taken in tetrahydrofuran (THF, 1.5 L). Dilute sulphuric acid (2N, 86 ml H$_2$SO$_4$ in 1430 ml water) was added and heated at reflux (85°) overnight. The reaction mixture was left for cooling and the product precipitated. The product was taken in dichloromethane and precipitated from hexane. Yield: 110 g (92%).

EXAMPLE 5

Synthesis of 2-(N-tert-butyl)-2'-(2-Indenyl)Biphenyl 2-(N-tert-butyl)-2'-(2-indenyl)biphenyl is synthesized according to scheme 6:

Scheme 6

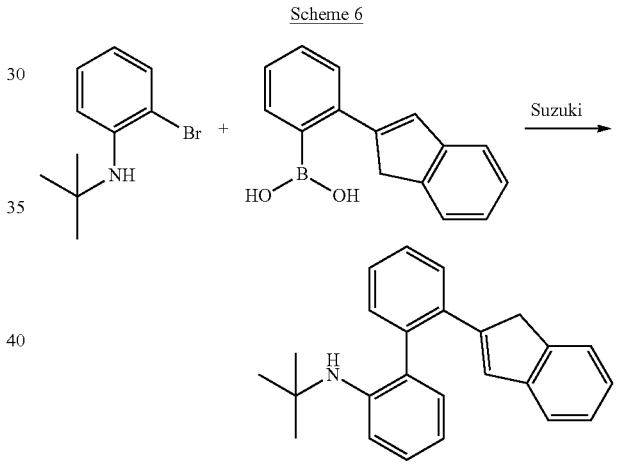

54 g (0.2358 moles) of N-tert-butyl-2-bromoaniline (prepared according to example 1) was dissolved in 500 ml of toluene and tetrakis triphenyl phosphine palladium was added (1.3644 g; 0.001 moles; 5 mol %). After 15 min, aqueous sodium carbonate (151 g; 1.426 moles (dissolved in 500 ml water)) was added followed by 2-(2-indenyl)phenylboronic acid (66.8 g; 0.283 moles) (prepared according to example 4). The reaction mixture was stirred at 115° C. overnight. Next day, the reaction mixture was cooled and the organic layer was separated. The organic layer was concentrated and purified by column using hexane: dichloromethane as eluent. Gradient: 0-20% of dichloromethane. Yield: 6.2 g (10%).

500 mg (0.0015 moles) of the ligand was weighed into one arm of a clean, dry double Schlenk (inside the glove box). The Schlenk was transferred into fumehood and N$_2$ atmosphere was applied. Freshly dried diethyl ether (15 ml) was added using a syringe. The sample was dissolved completely in diethyl ether. The solution was cooled to −78° C. n-BuLi (1.96 ml; 1.6N in hexanes; 0.00315 moles) was added to this solution drop wise. The color gradually changed to yellow and the solution became hazy with precipitation of yellow solid. The cold bath was removed after ~30 min and solution left to stir at RT for 4 hrs. The color of the solution became yellow and gradually changed to brown and greenish brown in about 2 h. The solution was again cooled to −78° C. and solid ZrCl4 (0.35 g; 0.0015 moles) was added. Immediately after the addition of ZrCl4, the color of the solution was changed to yellow. The temperature of the solution was slowly brought to RT and left the solution for stirring for 2 h. The color of the solution was turned to brown and solid was precipitated. Stopped the stirring and ether was taken to the other arm of the Schlenk by filtration. Solid was washed with ether and dried.

The invention claimed is:

1. A metallocene complex according to formula 1

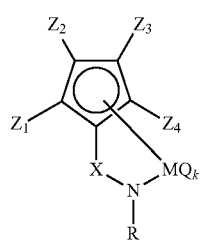

(1)

wherein
M is a lanthanide metal or a transition metal of group 3, 4, 5, or 6 of the Periodic System of the Elements;
Q is an anionic ligand to M;
k is the number of Q groups and equals the valence of M minus 2;
X is a cyclic bridging group;
$Z_1$ and $Z_4$ are identical or different and are hydrogen or a hydrocarbon radical with 1-20 carbon atoms;
adjacent substituents $Z_2$ and $Z_3$ are connected to form a 2-indenyl or 2-tetrahydroindenyl ring system together with the carbon atoms of the Cp ring to which they are bound; and
R is hydrogen or a hydrocarbon radical with 1-20 carbon atoms.

2. The metallocene complex according to claim 1, wherein the metal M is Ti, Zr, Hf, V, or Sm, and wherein Q is a halogen or a hydrocarbyl group comprising 1 to 20 carbon atoms.

3. The metallocene complex according to claim 1, wherein X is cyclopropylene, cyclobutylene, cyclopentylene, cyclohexylene, cyclohexenylene, cyclohexadienylene, tolylene, benzylene, naphthylene, anthrylene, pyrenylene, biphenylene or binaphthylene.

4. The metallocene complex according to claim 1, wherein the metallocene complex comprises a 2-indenyl group and is represented by formula 4

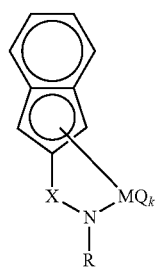

(4)

wherein
M is Ti, Zr, or Hf;
X is a cyclic bridging group;
R is hydrogen or a hydrocarbon radical with 1-20 carbon atoms;
Q is chlorine or a methyl group; and
k is the number of Q groups and equals the valence of M minus 2, wherein k is an integer.

5. The metallocene complex according to claim 4, wherein M is Zr; R is t-butyl; Q is chlorine or methyl; k=2; and X is phenylene, cyclopropylene, cyclobutylene, cyclopentylene, cyclohexylene, cyclohexenylene, cyclohexadienylene, tolylene, benzylene, naphthylene, anthrylene, pyrenylene, biphenylene or binaphthylene.

6. The metallocene complex according to claim 1, wherein the metallocene complex is present on a support.

7. A process for the preparation of the metallocene complex according to formula 5

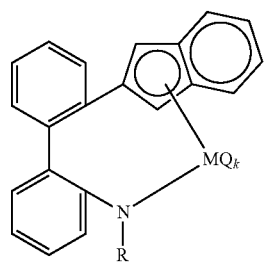

(5)

comprising:
a) reacting 2-bromophenyl boronic acid with 1,8-diaminonaphthalene to form a protected compound according to formula 13,

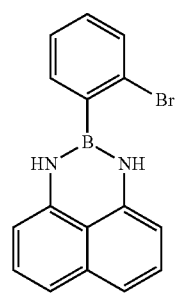

(13)

b) reacting the protected compound (13) with a compound according to formula 14,

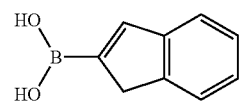

(14)

in the presence of a Pd catalyst and in the presence of a base to form a protected compound according to formula 15, (15)

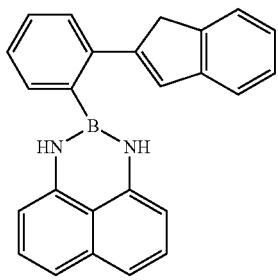

c) deprotecting the protected compound (15) by reaction with an acid to provide the compound according to formula 16, (16)

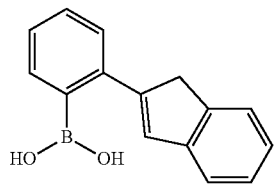

reacting the compound (16) with an N-substituted 2-bromoaniline in the presence of a Pd catalyst and in the presence of a base, to form a ligand precursor according to formula 11, wherein the N-substituted 2-bromoaniline is substituted with hydrogen or a hydrocarbon radical with 1-20 carbon atoms, d) creating an anion of the ligand precursor (11) with an organic or inorganic base, e) reacting the anion of the ligand precursor with $(Me_2N)_aMQ_k$, wherein Me is methyl; M is a lanthanide metal or a transition metal of group 3, 4, 5 or 6 of the Periodic System of the Elements; Q is an anionic ligand to M; k is the number of Q groups and equals the valence of M minus 2; and a equals the valence of M minus k, to yield a metallocene complex according to formula 5.

8. A process for the preparation of an olefin polymer, comprising polymerizing one or more olefins in the presence of the metallocene complex according to claim 1 and a cocatalyst.

9. The process according to claim 8, wherein the olefins comprise a mixture of ethylene and at least one other olefin of 3 or more carbon atoms.

10. The metallocene complex according to claim 1, wherein
the metal M is Ti, Zr, or Hf;
Q is a halogen or a hydrocarbyl group comprising 1 to 20 carbon atoms,
X is cyclopropylene, cyclobutylene, cyclopentylene, cyclohexylene, cyclohexenylene, cyclohexadienylene, tolylene, benzylene, naphthylene, anthrylene, pyrenylene, biphenylene or binaphthylene.

11. A process for the preparation of an olefin polymer, comprising polymerizing one or more olefins in the presence of the metallocene complex according to claim 10 and an aluminium- or boron-containing cocatalyst.

12. The metallocene complex according to claim 10, wherein X is a 2,2'-biphenylene group.

13. A process for the preparation of an olefin polymer, comprising polymerizing one or more olefins in the presence of the metallocene complex according to claim 12 and an aluminium- or boron-containing cocatalyst.

14. The method of claim 7, wherein
the N-substituted 2-bromoaniline is N-tert-butyl-2-bromoaniline;
the metal M is Ti, Zr, Hf, V, or Sm; and
Q is a halogen or a hydrocarbyl group comprising 1 to 20 carbon atoms.

15. The method of claim 12, wherein
the metal M is Zr;
Q is chlorine or a methyl; and
k=2.

* * * * *